United States Patent [19]
Seward et al.

[11] Patent Number: 6,059,731
[45] Date of Patent: May 9, 2000

[54] SIMULTANEOUS SIDE-AND-END VIEWING UNDERFLUID CATHETER

[75] Inventors: James Bernard Seward; Douglas L. Packer, both of Rochester, Minn.

[73] Assignee: Mayo Foundation for Medical Education and Research, Rochester, Minn.

[21] Appl. No.: 09/136,276

[22] Filed: Aug. 19, 1998

[51] Int. Cl.[7] .................................................. A61B 8/14
[52] U.S. Cl. .......................................... 600/459; 600/466
[58] Field of Search ..................................... 600/459, 444, 600/447, 463, 467, 473, 585, 466, 454, 468; 606/7, 15, 17; 607/89

[56] References Cited

U.S. PATENT DOCUMENTS

| | | |
|---|---|---|
| 3,789,833 | 2/1974 | Bom . |
| 3,817,089 | 6/1974 | Eggleton et al. . |
| 3,938,502 | 2/1976 | Bom . |
| 4,028,934 | 6/1977 | Sollish . |
| 4,110,723 | 8/1978 | Hetz et al. . |
| 4,354,502 | 10/1982 | Colley et al. . |
| 4,374,525 | 2/1983 | Baba . |
| 4,391,282 | 7/1983 | Ando et al. . |
| 4,462,408 | 7/1984 | Silverstein et al. . |
| 4,466,444 | 8/1984 | Baba . |
| 4,543,960 | 10/1985 | Harui et al. . |
| 4,550,607 | 11/1985 | Maslak et al. . |
| 4,582,067 | 4/1986 | Silverstein et al. . |
| 4,699,009 | 10/1987 | Maslak et al. . |
| 4,748,985 | 6/1988 | Nagasaki . |
| 4,756,313 | 7/1988 | Terwilliger . |
| 4,757,821 | 7/1988 | Snyder . |
| 4,771,788 | 9/1988 | Millar . |
| 4,794,931 | 1/1989 | Yock . |
| 4,802,487 | 2/1989 | Martin et al. . |
| 4,841,977 | 6/1989 | Griffith et al. . |
| 4,841,979 | 6/1989 | Dow et al. . |
| 4,869,256 | 9/1989 | Kanno et al. . |

(List continued on next page.)

FOREIGN PATENT DOCUMENTS

| | | |
|---|---|---|
| 0 234 951 | 9/1987 | European Pat. Off. . |
| 0 600 568 A1 | 6/1994 | European Pat. Off. . |
| 0 642 762 A2 | 3/1995 | European Pat. Off. . |
| 44 23 808 A1 | 1/1995 | Germany . |
| WO 90/13260 | 11/1990 | WIPO . |
| WO 91/04707 | 4/1991 | WIPO . |
| WO 93/08738 | 5/1993 | WIPO . |
| WO 94/16625 | 8/1994 | WIPO . |
| WO 95/13111 | 5/1995 | WIPO . |
| WO 95/19143 | 7/1995 | WIPO . |
| WO 96/00522 | 1/1996 | WIPO . |
| WO 96/03918 | 2/1996 | WIPO . |
| WO 96/03921 | 2/1996 | WIPO . |
| WO 96/03922 | 2/1996 | WIPO . |
| WO 96/04588 | 2/1996 | WIPO . |

OTHER PUBLICATIONS

Lam, J. et al., "Transesophageal Echocardiography with the Use of a Four–Millimeter Probe", *Journal Am. Soc. of Echocardiography*, 10(5):499–504 (Jun. 1997).

McCann, H.A. et al., "Multidimensional Ultrasonic Imaging for Cardiology", Proc IEEE, 76(9):1063–1071 (Sep. 1988).

Bom, N. et al., "Early and Recent Intraluminal Ultrasound Devices", *International Journal of Cardiac Imaging*, 4:79–88 (1989).

(List continued on next page.)

*Primary Examiner*—Francis J. Jaworski
*Assistant Examiner*—Ali M. Imam
*Attorney, Agent, or Firm*—Merchant & Gould P.C.

[57] ABSTRACT

A simultaneous side-and-end viewing ultrasound imaging catheter system includes at least one side array and at least one end array. Each of the arrays has at least one row of ultrasonic transducer elements. The elements are operable as a single ultrasound transducer which are phased to produce a field of side-and-end view. A multiplanar omnidirectional field of side-and-end view can also be formed when there are a plurality of side arrays and end arrays mounted on the catheter body. In certain applications, the output of each array or a portion of an array can be separately displayed and/or interrogated so as to provide better navigational and therapeutic visual aids.

8 Claims, 4 Drawing Sheets

U.S. PATENT DOCUMENTS

| | | |
|---|---|---|
| 4,869,258 | 9/1989 | Walter Hetz . |
| 4,887,605 | 12/1989 | Angelsen et al. . |
| 4,911,170 | 3/1990 | Thomas, III et al. . |
| 4,917,097 | 4/1990 | Proudian et al. . |
| 4,930,515 | 6/1990 | Terwilliger . |
| 4,936,281 | 6/1990 | Stasz . |
| 4,947,852 | 8/1990 | Nassi et al. . |
| 4,951,677 | 8/1990 | Crowley et al. . |
| 4,957,111 | 9/1990 | Millar . |
| 5,000,185 | 3/1991 | Yock . |
| 5,002,059 | 3/1991 | Crowley et al. . |
| 5,010,886 | 4/1991 | Passafaro et al. . |
| 5,014,710 | 5/1991 | Maslak et al. . |
| 5,022,399 | 6/1991 | Biegeleisen . |
| 5,029,588 | 7/1991 | Yock et al. . |
| 5,038,789 | 8/1991 | Frazin . |
| 5,070,879 | 12/1991 | Herres . |
| 5,076,278 | 12/1991 | Vilkomerson et al. . |
| 5,076,279 | 12/1991 | Arenson et al. . |
| 5,081,993 | 1/1992 | Kitney et al. . |
| 5,085,221 | 2/1992 | Ingebrigtsen et al. . |
| 5,105,819 | 4/1992 | Wollschläger et al. . |
| 5,107,844 | 4/1992 | Kami et al. . |
| 5,115,814 | 5/1992 | Griffith et al. . |
| 5,125,410 | 6/1992 | Misono et al. . |
| 5,135,001 | 8/1992 | Sinofsky et al. . |
| 5,140,558 | 8/1992 | Harrison, Jr. et al. . |
| 5,148,810 | 9/1992 | Maslak et al. . |
| 5,152,294 | 10/1992 | Mochizuki et al. . |
| 5,159,931 | 11/1992 | Pini . |
| 5,161,537 | 11/1992 | Hashimoto et al. . |
| 5,165,413 | 11/1992 | Maslak et al. . |
| 5,174,296 | 12/1992 | Watanabe et al. . |
| 5,181,514 | 1/1993 | Solomon et al. . |
| 5,183,048 | 2/1993 | Eberle . |
| 5,186,175 | 2/1993 | Hirama et al. . |
| 5,186,177 | 2/1993 | O'Donnell et al. . |
| 5,193,546 | 3/1993 | Shaknovich . |
| 5,199,433 | 4/1993 | Metzger et al. . |
| 5,199,437 | 4/1993 | Langberg . |
| 5,211,168 | 5/1993 | Mason et al. . |
| 5,215,092 | 6/1993 | Wray . |
| 5,222,501 | 6/1993 | Ideker et al. . |
| 5,226,422 | 7/1993 | McKeighen et al. . |
| 5,235,986 | 8/1993 | Maslak et al. . |
| 5,243,988 | 9/1993 | Sieben et al. . |
| 5,257,629 | 11/1993 | Kitney et al. . |
| 5,261,408 | 11/1993 | Maslak et al. . |
| 5,285,788 | 2/1994 | Arenson et al. . |
| 5,291,893 | 3/1994 | Slayton . |
| 5,295,486 | 3/1994 | Wollschläger et al. . |
| 5,297,553 | 3/1994 | Sliwa, Jr. et al. . |
| 5,299,578 | 4/1994 | Rotteveel et al. . |
| 5,305,755 | 4/1994 | Nakao . |
| 5,305,756 | 4/1994 | Entrekin et al. . |
| 5,311,871 | 5/1994 | Yock . |
| 5,313,949 | 5/1994 | Yock . |
| 5,320,104 | 6/1994 | Fearnside et al. . |
| 5,325,860 | 7/1994 | Seward et al. . |
| 5,329,496 | 7/1994 | Smith . |
| 5,329,927 | 7/1994 | Gardineer et al. . |
| 5,343,865 | 9/1994 | Gardineer et al. . |
| 5,345,940 | 9/1994 | Seward et al. . |
| 5,351,691 | 10/1994 | Brommersma . |
| 5,360,007 | 11/1994 | Shinomura et al. . |
| 5,373,845 | 12/1994 | Gardineer et al. . |
| 5,373,849 | 12/1994 | Maroney et al. . |
| 5,377,685 | 1/1995 | Kazi et al. . |
| 5,385,148 | 1/1995 | Lesh et al. . |
| 5,398,689 | 3/1995 | Connor et al. . |
| 5,402,793 | 4/1995 | Gruner et al. . |
| 5,415,175 | 5/1995 | Hanafy et al. . |
| 5,421,336 | 6/1995 | De Bernardis . |
| 5,425,370 | 6/1995 | Vilkomerson . |
| 5,437,283 | 8/1995 | Ranalletta et al. ............ 600/463 |
| 5,438,997 | 8/1995 | Sieben et al. . |
| 5,438,998 | 8/1995 | Hanafy . |
| 5,460,181 | 10/1995 | Seyed-Bolorforsh . |
| 5,464,016 | 11/1995 | Nicholas et al. . |
| 5,465,724 | 11/1995 | Sliwa, Jr. et al. . |
| 5,467,779 | 11/1995 | Smith et al. . |
| 5,469,852 | 11/1995 | Nakamura et al. . |
| 5,474,075 | 12/1995 | Goldberg et al. . |
| 5,479,929 | 1/1996 | Cooper et al. . |
| 5,479,930 | 1/1996 | Gruner et al. . |
| 5,485,846 | 1/1996 | Webler et al. . |
| 5,487,388 | 1/1996 | Rello et al. . |
| 5,499,630 | 3/1996 | Hiki et al. . |
| 5,503,152 | 4/1996 | Oakley et al. . |
| 5,549,111 | 8/1996 | Wright et al. . |
| 5,562,095 | 10/1996 | Downey et al. . |
| 5,569,276 | 10/1996 | Jang et al. . |
| 5,630,416 | 5/1997 | Urchikura et al. . |
| 5,634,464 | 6/1997 | Jang et al. . |
| 5,697,377 | 12/1997 | Wittkampf . |
| 5,699,805 | 12/1997 | Seward et al. . |
| 5,704,361 | 1/1998 | Seward et al. . |
| 5,713,363 | 2/1998 | Seward et al. . |
| 5,749,833 | 5/1998 | Hakki et al. . |

OTHER PUBLICATIONS

Bom, N. et al., "Intravascular Ultrasound: Newest Branch of the Echo–Tree", *Cardiovascular Imaging*, 4:55–59 (1992).

Devonald, K.J. et al., "Volume Imaging: Three–Dimensional Appreciation of the Fetal Head and Face", *J. Ultrasound Med.*, 14:919–925 (1995).

Entrekin, R. et al., "Real–Time 3–D Ultrasound Imaging with a 1–D 'Fan Beam' Transducer Array", *SPIE*, 1733:264–272 (1992).

F–D–C Reports, Inc., "Cardiovascular Imaging Systems' Intracardiac Imagining Catheter", *M–D–D–I Reports*, pp. I &W–6 and I&W–7 (Mar. 30, 1992).

Hung, J. et al., "Usefulness of Intracardiac Echocardiography in Transseptal Puncture During Percutaneous Transvenous Mitral Commissurotomy", *Section of Cardiology, Chang Gung Medical College and Chang Gung Memorial Hospital*, p. 853 (May 10, 1993).

Kossoff, G. et al., "Real–Time Quasi–Three–Dimensional Viewing in Sonography, with Conventional, Gray–Scale Volume Imaging", *Ultrasound Obstet. Gynecol.*, 4:211–216 (1994).

Kremkau, F.W., "AAPM Tutorial. Multiple–Element Transducers", *Radiographics*, pp. 1163–1176 (Sep. 1993).

Moriuchi, M. et al., "Transvenous Echocardiography: Experimental Feasibility Study", *Jpn J Med Ultrasonics*, 19(3):228–235 (1992).

Nishimura, R.A. et al., "Intravascular Ultrasound Imaging: In Vitro Validation and Pathologic Correlation", *JACC*, 16(1):145–154 (Jul. 1990).

Pandian, N.G. et al., "Intracardiac, Intravascular, Two–Dimensional, High–Frequency Ultrasound Imaging of Pulmonary Artery and Its Branches in Humans and Animals", *Circulation*, 81(6):2007–2012 (Jun. 1990).

Pandian, N.G. et al., "Intracardiac Echocardiography Experimental Observations on Intracavitary Imaging of Cardiac Structures with 20–MHz Ultrasound Catheters", *Echocardiography*, 8:127–134 (Jan. 1991).

Pandian, N.G. et al., "Real–Time, Intracardiac, Two–Dimensional Echocardiography. Enhanced Depth of Field with a Low–Frequency (12.5 MHz) Ultrasound Catheter", *Echocardiography*, 8(4):407–422 (1991).

Papavasassiliou, D. et al., "Initial Experience with an Internally Rotating Transthoracic Three–Dimensional Exhocardiographic Probe and Image Acquistion on a Conventional Echocardiogram Machine", *Echocardiography: A Jrnl. of CB Ultrasound& Allied Tech.*, vol. 15, No. 4, 1998.

Rothman, A. et al., "Intraluminal Ultrasound Imaging Through a Balloon Dilation Catheter in an Animal Model of Coarctation of the Aorta", *Circulation*, 85(6):2291–2295 (Jun. 1992).

Schwartz, S. et al., "Intracardiac Echocardiographic Guidance and Monitoring During Aortic and Mitral Balloon Valvuloplasty: In Vivo Experimental Studies", Abstract, *JACC*, 15(2):104A (Feb. 1990).

Schwartz, S.L. et al., "Real–Time Intracardiac Two–Dimensional Echocardiography: An Experimental Study of In Vivo Feasibility, Imaging Planes, and Echocardiographic Anatomy", *Echocardiography*, 7(4):443–455 (Jul. 1990).

Schwartz, S.L. et al., "Intracardiac Echocardiography During Simulated Aortic and Mitral Balloon Valvuloplasty: In Vivo Experimental Studies", *Am. Heart Journal*, 123(3):665–674 (Mar. 1992).

Schwartz, S.L. et al., "Intracardiac Echocardiography in Humans Using a Small–Sized (6F), Low Frequency (12.5 MHz) Ultrasound Catheter", *JACC*, 21(1):189–198 (Jan. 1993).

Schwartz, S.L. et al., "Intracardiac Echocardiographic Imaging of Cardiac Abnormalities, Ischemic Myocardial Dysfunction, and Myocardial Perfusion: Studies With a 10 MHz Ultrasound Catheter", *Journal Am Soc. of Echocardiography*, 6(4):345–355 (Jul.–Aug. 1993).

Schwartz, S.L. et al., "Intracardiac Echocardiography Without Fluoroscopy: Potential of a Balloon–Tipped, Flow–Directed Ultrasound Catheter", *Am. Heart Journal*, 129(3):598–603 (Mar. 1995).

Seward, J.B. et al., "Transvascular and Intracardiac Two–Dimensional Echocardiography", *Echocardiography*, 7(4):457–464 (Jul. 1990).

Seward, J.B., et al., "Multiplane Transesophageal Echocardiography: Image Orientation, Examination Technique, Anatomic Correlations, and Clinical Applications", *Mayo Clin Proc.,*68:523–551 (Jun. 1993).

Seward, J.B. et al., "Ultrasound Cardioscopy: Embarking on a New Journey", *Mayo Clin Proc.*, 71(7):629–635 (Jul. 1996).

Smith, S.W. et al., "High–Speed Ultrasound Volumetric Imaging System–Part I: Transducer Design and Beam Steering", *IEEE Transactions on Ultrasonics, Ferroelectrics, and Frequency Control*, 38(2):100–108 (Mar. 1991).

Talbert, D.G., "An 'Add–On' Modification for Linear Array Real Time Ultrasound Scanners to Produce 3 Dimensional Displays", Conference: Ultrasonics International 1977. Brighton, England, pp. 52–67 (Jun. 28–30 1997).

Tardif, J., et al., "Intracardiac Echocardiography With a Steerable Low–Frequency Linear–Array Probe for Left–Sided Heart Imaging from the Right Side; Experimental Studies" *Journal Am. Soc. of Echocardiography*, 8(2):132–138 (Mar.–Apr. 1995).

von Ramm, O.T. et al., "High–Speed Ultrasound Volumetric Imaging System–Part II: Parallel Processing and Image Display", *IEEE Transactions on Ultrasonics, Ferroelectrics, and Frequency Control*, 38(2):109–115 (Mar. 1991).

Weintraub, A. et al., "Realtime Intracardiac Two–Dimensional Echocardiography in the Catheterization Laboratory in Humans". Abstract *JACC*, 15(2):16A (Feb. 1990).

Weintraub, A.R. et al., "Intracardiac Two–dimensional Echocardiography in Patients with Pericardial Effusion and Cardiac Tamponade", *Journal Am Soc. of Echocardiography*, 4(6):571–576 (Nov.–Dec. 1991).

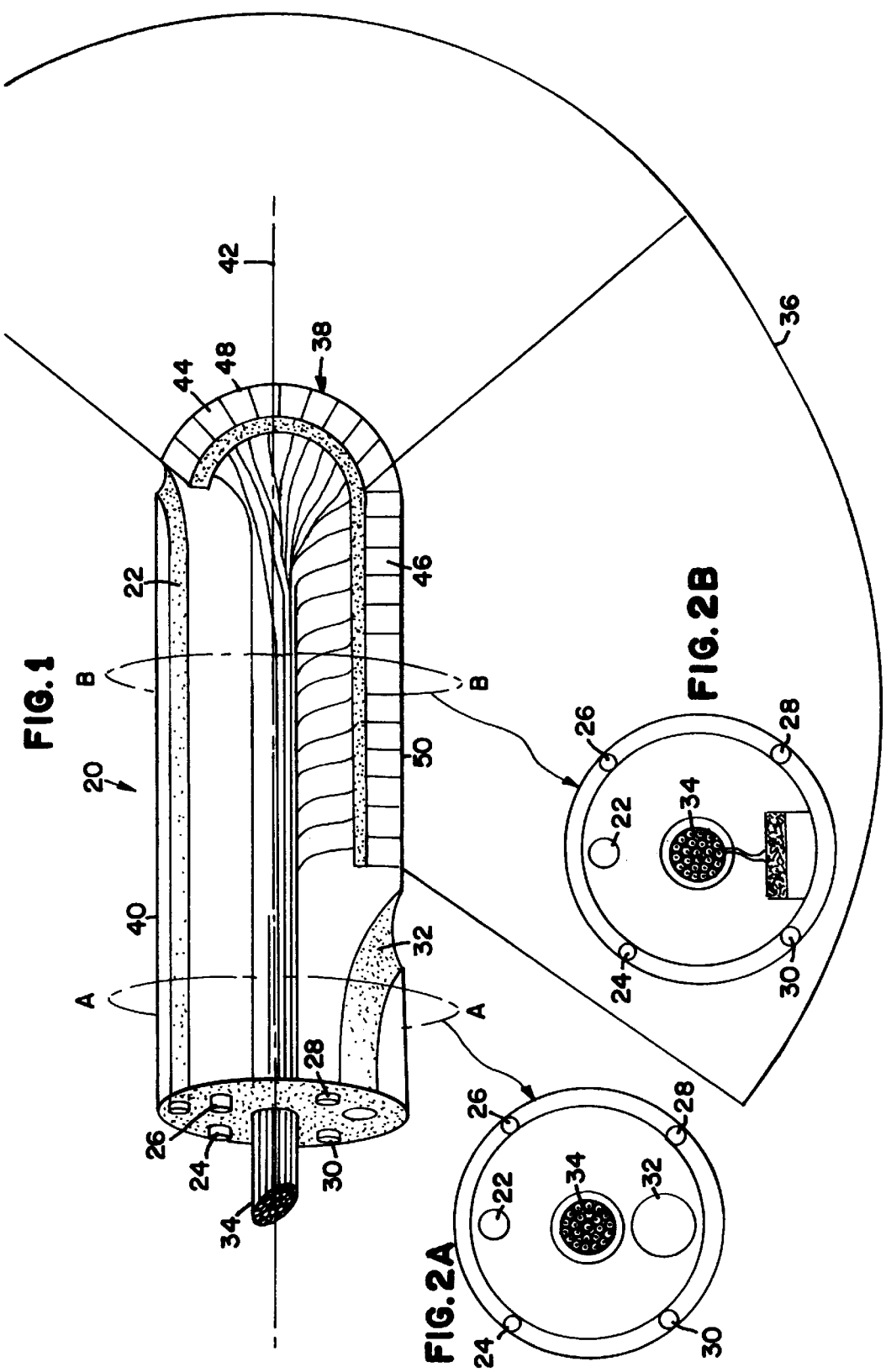

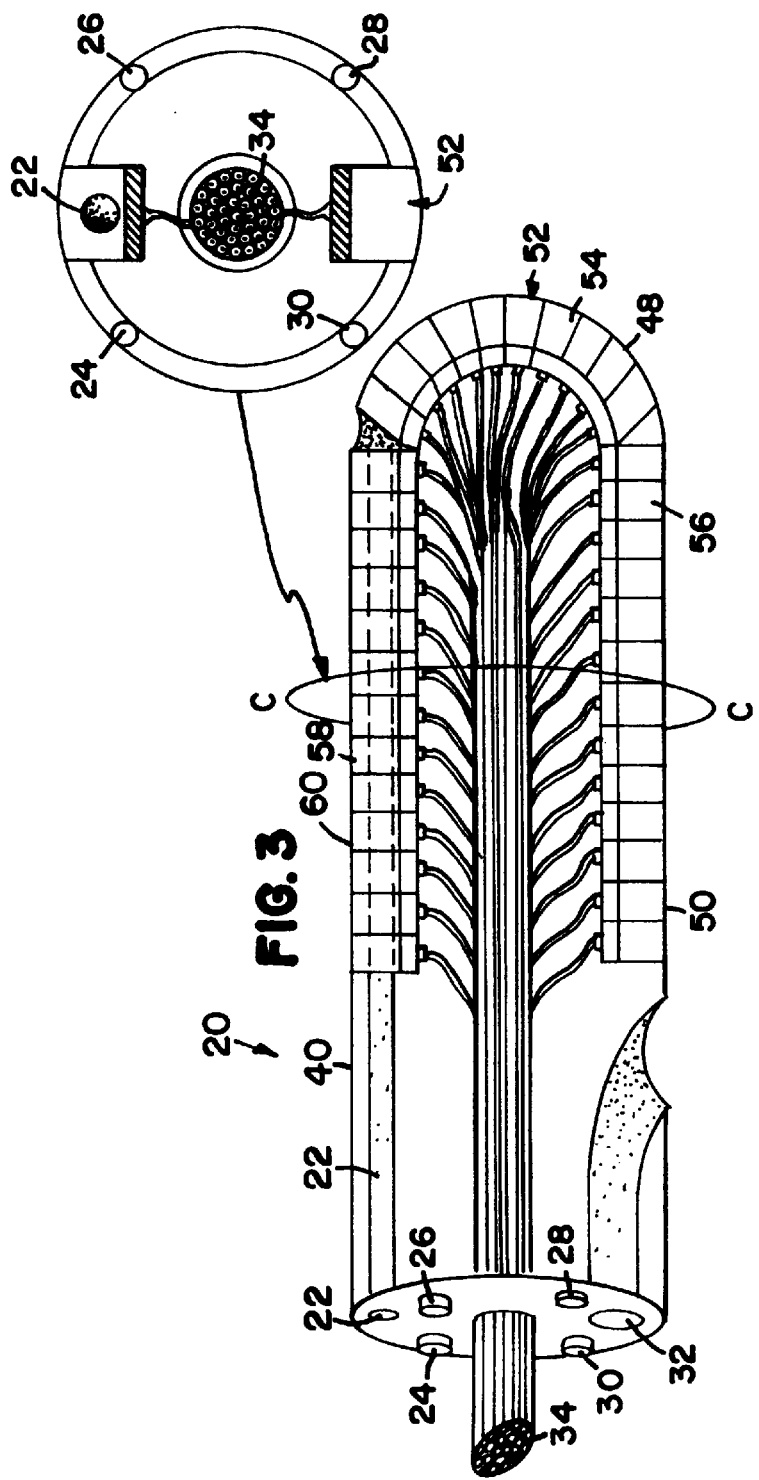

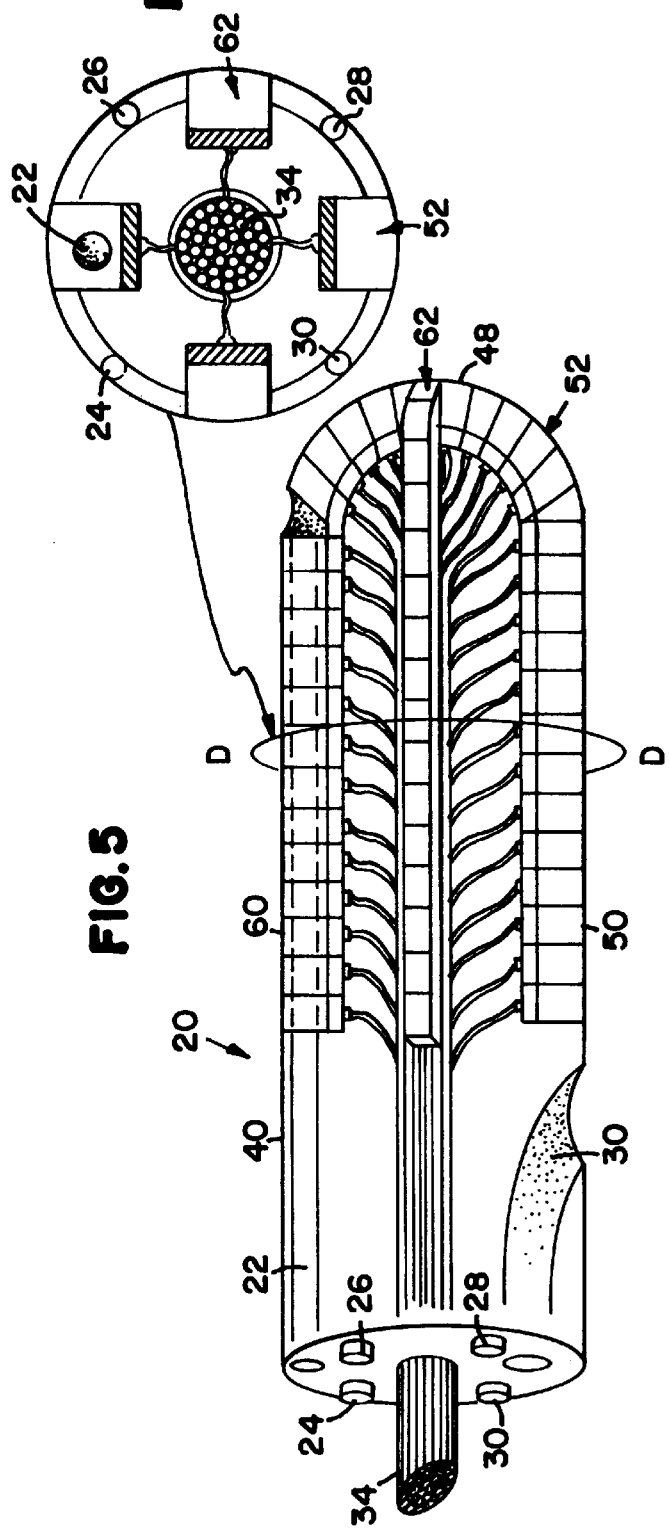

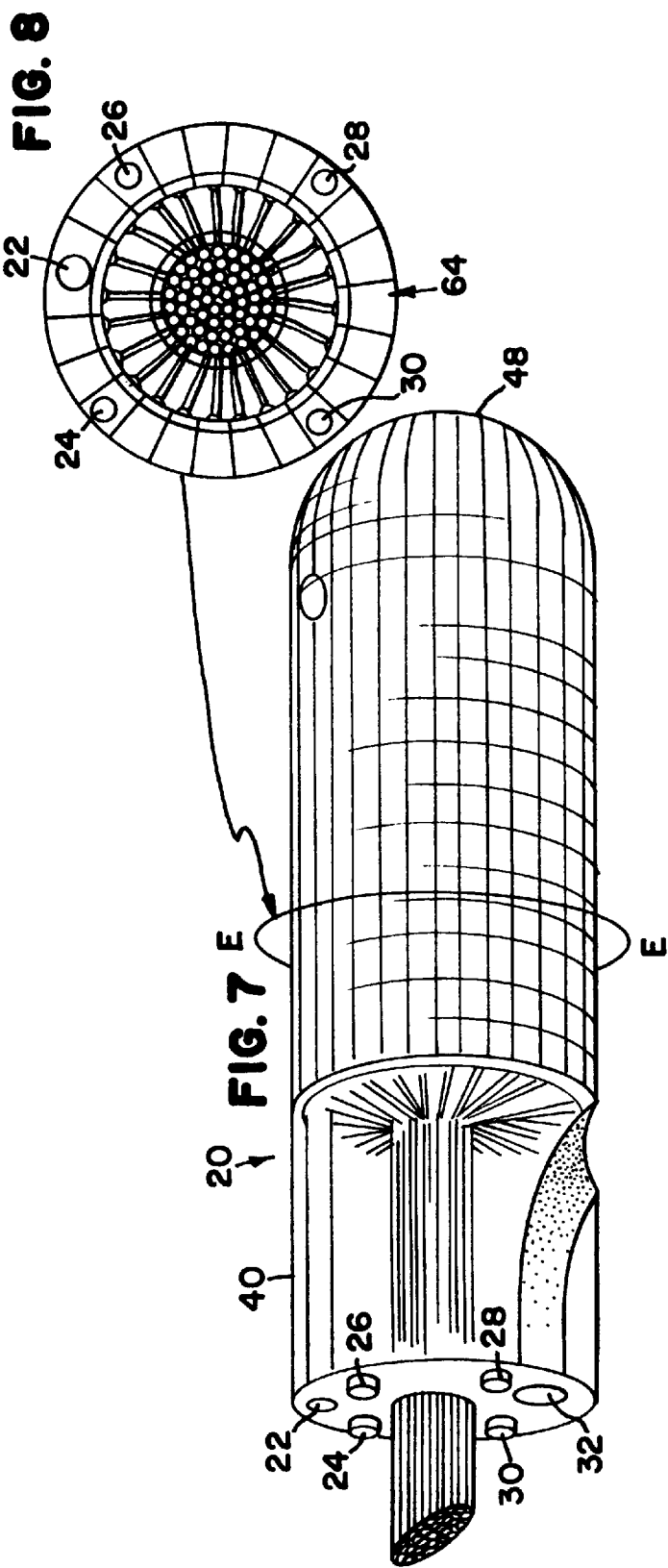

SIMULTANEOUS SIDE-AND-END VIEWING UNDERFLUID CATHETER

INCORPORATION OF RELATED APPLICATIONS

The present invention relates to U.S. patent application Ser. No. 08/678,380, filed Jun. 28, 1996, now issued U.S. Pat. No. 5,704,361, issued on Jan. 6, 1998; which is a continuation-in-part application of U.S. patent application Ser. No. 08/636,916, filed Apr. 24, 1996, now issued U.S. Pat. No. 5,713,363, issued on Feb. 3, 1998; which is a File-Wrapper-Continuation application of U.S. patent application Ser. No. 08/305,138, filed Sep. 13, 1994, now abandoned; which is a continuation application of U.S. patent application Ser. No. 07/972,626, filed Nov. 6, 1992, now issued U.S. Pat. No. 5,345,940, issued on Sep. 13, 1994; which is a continuation-in-part application of U.S. patent application Ser. No. 07/790,580, filed on Nov. 8, 1991, now issued U.S. Pat. No. 5,325,860, issued on Jul. 5, 1994; the subject matter of which are incorporated by reference.

BACKGROUND OF THE INVENTION

Ultrasound is an ideal imaging modality for underfluid navigation, diagnosis, and therapy. Larger fields of view will enhance application and versatility of these functions. Current ultrasound catheters typically view in only one direction, either to the side or forward. Previous invention disclosures of ultrasound catheters, by Seward, et al. of the above listed patents, capable of viewing in more than one direction have used individual piezoelectric elements which have a limited field of view, e.g., (1) linear array of individual elements (rectangular shaped image), (2) oscillating (i.e., nutate) element (sector shaped image with limited penetration), or (3) rotating element with reflecting mirror. Current ultrasound catheters also characteristically have high frequency transducer elements with limited penetration, which are principally used for imaging vessels (e.g., most typically the coronary arteries or peripheral veins and arteries), and have only incidentally been used for intra-cavitary imaging.

Accordingly, there is a need in ultrasound imaging catheter industry for a catheter providing a wide field of view, especially a wide field of view for underfluid navigation, diagnosis, and therapy.

SUMMARY OF THE INVENTION

The present invention relates generally to an ultrasound imaging catheter system and method, more particularly, a simultaneous side-and-end viewing ultrasound imaging catheter system and method which provides a wide field of view for underfluid navigation, diagnosis, and therapy.

In one embodiment of the present invention, a sector phased-array (e.g. linear sector, i.e., one-dimensional array (a single row of ultrasonic transducer elements); one-and-one-half dimensional array (the number of columns and rows of ultrasonic transducer elements has a great disparity); and a two-dimensional array in general (multiple columns and rows of ultrasonic transducer elements, e.g. a square shaped array); etc.) is comprised of extremely closely spaced piezoelectric elements which, when stimulated, act as a single ultrasound transducer which can be stimulated (phased) to produce a wide field of view. The image field is directed beyond the mere area of the transducer array surface (e.g. sector shaped image or volumetric shaped image, etc.).

Still in one embodiment of the present invention, the phased array has an azimuthal plane (usually along a longitudinal axis of a catheter) and an elevational plane (usually perpendicular to the azimuthal plane). In the azimuthal plane, ultrasound beams are displayed in a pie shape with an angle, for example 90°. Similarly, in the elevation plane, the ultrasound beams can be directed outward forming a volumetric field of view (e.g. 3-dimensional image field having length, height, and width). Further, the ultrasound transducers have a comparatively deep field of penetration, producing large tomographic (two-dimensional) or volumetric (three-dimensional) image fields suitable for imaging within any fluid-filled cavity (e.g. heart, urinary bladder, etc.), large vessels, or imaging areas beyond the confines of the cavity (e.g. transvascular imagery).

The present invention also provides a method of optimizing image presentation by incorporating variably sized arrays for simultaneous side-view and end-view. In general, a catheter has small surface areas in which to incorporate sets of ultrasound elements or arrays. Accordingly, there is a compromise between the size of the catheter's diameter and the number of element groupings incorporated. As a result, a field of view varies depending upon an array configuration and an obligatory size of the catheter.

In one embodiment of the present invention, the variable sized arrays are configured and arranged at side and end of the catheter, and the image presentation is optimized by incorporating the variable sized arrays for simultaneous side-viewing and end-viewing. Accordingly, one of the unique features of the present invention is the use of phased sector arrays to a catheter with simultaneous side-and-end view ultrasound imaging.

One advantage of the present invention is that the side-and-end viewing ultrasound catheter permits simultaneous imaging in both the lateral and forward directions of the catheter. Forward viewing assists principally in navigating in the forward direction while observing, performing, or directing events in front of the catheter. The side-view is principally used for observing events in a longitudinal axis of the catheter and/or for fostering the performing of the functions adjacent to a catheter shaft. Further, fields of views can be utilized separately or simultaneously, can monitor events within adjacent cavities or outside a chamber or vessel. An example of simultaneous view is the use of the forward image to navigate through an irregularly shaped vessel or chamber and observing therapeutic functions in a lateral field of view in real time.

In one embodiment of the present invention, a catheter apparatus includes an elongated body having a longitudinal axis; an ultrasonic transducer side array having at least one row of ultrasonic transducer elements mounted on the body along a first side of the body; an ultrasonic transducer end array having at least one row of ultrasonic transducer elements mounted on the body at a forward end of the body; and each of the ultrasonic transducer elements of the side array and the end array being operable as a single ultrasound transducer which are phased to produce a field of side-and-end view.

Further in one embodiment of the present invention, the ultrasonic transducer side and end arrays include a piezoelectric polymer material. Alternatively, the ultrasonic transducer side and end arrays include a polyvinylidenedifloride (PVDF) material.

Still in one embodiment of the present invention, the catheter body has a diameter of 4 to 15 French.

Yet in one embodiment of the present invention, the catheter body has a length 20 to 120 cm.

Further in one embodiment of the present invention, the catheter apparatus further includes a second ultrasonic transducer side array having at least one row of ultrasonic transducer elements mounted on the body along a second side of the body, wherein the first and second side arrays are longitudinally mounted on the body.

Still in further one embodiment of the present invention, the ultrasonic transducer end array and the first and second ultrasonic transducer side arrays are disposed in a single plane, each of the ultrasonic transducer elements of the ultrasonic transducer end array and the first and second side arrays are operable as a single ultrasound transducer which are phased to produce a field of side-and-end view.

Yet in further one embodiment of the present invention, the catheter apparatus further includes a second ultrasonic transducer end array and third and fourth ultrasonic transducer side arrays which are disposed in a second plane, wherein each of the ultrasonic transducer elements of the first, second, third, and fourth side arrays and the first and second end arrays are operable as a single ultrasound transducer which are phased to produce a biplanar field of side-and-end view.

The present invention also provides a catheter apparatus which includes an elongated body having a longitudinal axis; a plurality of ultrasonic transducer side arrays each having at least one row of ultrasonic transducer elements mounted on the body along corresponding a plurality of sides of the body; a plurality of ultrasonic transducer end arrays each having at least one row of ultrasonic transducer elements mounted on the body at a forward end of the body; and each of the ultrasonic transducer elements of the side arrays and the end arrays being operable as a single ultrasound transducer which are phased to produce a multiplanar omnidirectional field of side-and-end view.

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

A better understanding of the construction and operational characteristics of a preferred embodiment(s) can be realized from a reading of the following detailed description, especially in light of the accompanying drawings in which like reference numerals in the several views generally refer to corresponding parts.

FIG. 1 is a partial perspective and longitudinal cross-sectional view of an embodiment of a catheter in accordance with the principles of the present invention.

FIG. 2A is a transversal cross-sectional view from line A—A of FIG. 1.

FIG. 2B is a transversal cross-sectional view from line B—B of FIG. 1.

FIG. 3 is a partial perspective and longitudinal cross-sectional view of a second embodiment of the catheter in accordance with the principles of the present invention.

FIG. 4 is a transversal cross-sectional view from line C—C of FIG. 3.

FIG. 5 is a partial perspective and longitudinal cross-sectional view of a third embodiment of the catheter in accordance with the principles of the present invention.

FIG. 6 is a transversal cross-sectional view from line D—D of FIG. 5.

FIG. 7 is a partial perspective and longitudinal cross-sectional view of a fourth embodiment of the catheter in accordance with the principles of the present invention.

FIG. 8 is a transversal cross-sectional view from line E—E of FIG. 7.

DETAILED DESCRIPTION OF THE PREFERRED EMBODIMENTS

The present invention relates to an ultrasound imaging catheter system and method, more particularly, a simultaneous side-and-end viewing ultrasound imaging catheter system and method which provides a wide field of view for underfluid navigation, diagnosis, and therapy.

In the following description of the exemplary embodiment, reference is made to the accompanying drawings which form a part hereof, and in which is shown by way of illustration the specific embodiment in which the invention may be practiced. It is to be understood that other embodiments may be utilized as structural changes may be made without departing from the scope of the present invention.

Referring now to FIGS. 1, 2A, 2B, there is, generally illustrated by reference numeral 20, a catheter in accordance with the principles of the present invention. It is appreciated that the detailed catheter features and control circuitry of the catheter have been disclosed in the above previous patents listed above, the subject of which are incorporated by reference. For purpose of illustration, some generic catheter features are shown and briefly discussed, but not limited, below. It is appreciated to a person skilled in the art that these features may or may not be incorporated into an embodiment of a catheter of the present invention.

- Guidewire port: a small internal channel extending the length of the catheter (e.g. from a proximate end to a distal end of the catheter) through which variably sized wires are introduced. Guide wires are used to assist in directing, defecting, or merely changing the position, tension/torque, or configuration of the catheter tip. Typically, a guidewire port exits near the distal end of the catheter and enters at the proximal end of the catheter.
- Additional ports: frequently, additional channels are incorporated into the catheter through which functions such as pressure monitoring, administration of agents (i.e., contrast, drugs, etc.), or other tools/devices can be introduced.
- Portless catheter: some ultrasound catheters have no need for guidewire or other delivery/monitoring ports.
- Flexible shaft/tip and multi-directional control: through various techniques (e.g. cables, controls, etc., which extend from the proximal end to the distal end of the catheter, are incorporated into an outer wall of the catheter), the shaft or the distal end (i.e., tip) of the catheter can be manipulated. Because of the environment (e.g., small fluid-filled cavities), such control mechanisms assist in obtaining an optimized catheter position. The catheter has variable stiffness (bendability) and twist (torque or memory) features—depending on the application.
- Catheter length (preferred 20–120 cm): A catheter length is designed depending on the application of a catheter, for example, depending on an entry site (e.g., femoral vessel vs. arm vs. neck), or size of the patient, or site of operation (i.e., right heart vs. left heart vs. abdominal vessel). The catheter length can be optimized for the specific application. In one preferred embodiment, the catheter length is 20–120 cm. It is appreciated to a skilled person in the art that other catheter lengths can be used without departure from the principles and scope of the present invention. For example, in one embodiment the catheter length might range from 10–150 cm.

Catheter diameter (preferred 4 to 15 French): diameter of a catheter can vary depending on the number of functions incorporated and the state of technological miniaturization. Catheters of larger caliber are most often used in venous vessels or large cavities such as the urethra or esophagus. Small caliber catheters are more often used in arteries or small cavities of the body (example: ureter). In one preferred embodiment, the catheter diameter is 4 to 15 French. It is appreciated to a person skilled in the art that other catheter diameters can be used without departure from the principles and scope of the present invention. For example, in one embodiment the catheter diameter might range from 4 to 24 French.

As shown in FIGS. 1, 2A, and 2B, there are a guidewire port 22, four wire cables 24,26,28,30 for controls, a tool/device port 32, and electrical conductors 34 which connect the ultrasonic transducer array to a control unit external to the catheter 20. It is appreciated that many suitable connecting arrangements between the ultrasonic transducer array and the electrical conductors can be used within the scope of the present invention. For example, in one embodiment, the electrical conductors might directly connect to the ultrasonic transducer array (in the preferred embodiment). In an alternative embodiment, the electrical conductors might connect to the ultrasonic transducer array via a functional unit, such as an amplifier, etc. It is also appreciated that any other suitable control arrangements between the ultrasonic transducer array and the control unit can be used within the scope of the present invention. For example, a wireless control between the control unit and the ultrasonic transducer array can be implemented. Similar features can be incorporated in alternative embodiments shown in FIGS. 3, 5, and 7. A guide wire (not shown) can be extended from a proximate end of the catheter to a distal end of the catheter via the guidewire port 22. A tool/device port 32 can deliver a tool (not shown), such as a therapeutic device, or a measuring/monitoring tool, etc., into a field of view 36 (only a plane view is illustrated) formed by ultrasonic transducer arrays 38. Further, the catheter 20 has an elongated body 40 having a longitudinal axis 42.

The ultrasonic transducer arrays 38 is preferably a phased array. In one embodiment, the basic image technology (i.e., multi-element transducer with electronically driven variable field of view) can be attained with a family of transducer element arrangements and electronic imaging solutions. In the preferred embodiment, phased array transducer piezoelectric elements are closely aligned and phased (send/receive) to variably configure the field of view. Such transducer arrays can be configured, arranged, stimulated, lensed, focused or moved in a manner to create variable fields of view. Various transducer types can be used in the present invention. Some of the exemplary types are briefly discussed, but not limited, below. The detailed discussions of the below types of array transducer are referred to the above listed patents and U.S. Pat. No. 5,699,805, to Dr. Seward, et al., issued on Dec. 23, 1997. It is appreciated to a person skilled in the art that any other transducer types can be used within the principles and scope of the present invention.

Sector-phased array transducer (preferred): closely aligned ultrasound piezoelectric elements (i.e., linear in shape) are electronically stimulated in a manner such that the array of individual elements function as a single unit. As a single unit, the sound beam can be electronically directed beyond the mere configuration of the array surface (i.e., beyond a rectangular shape). The most typical beam configuration 36 is a pie-shape of various azimuthal dimension infrequently exceeding 90°s of tomographic view.

1.5- and 2-dimensional array transducer: by placing multiple rows of elements close together, the ultrasound beam can be spread outward not only in the azimuthal dimension but also in the plane perpendicular to the array (i.e., in an elevation dimension). The 1.5-dimensional array is a set of piezoelectric elements shaped like a long rectangle, and a 2-dimensional array is shaped like a short rectangle or a square. By expanding the beam in the azimuthal and elevational planes, a volume of tissue/fluid, etc., can be simultaneously insonsated in a volumetric field of view.

Transducer lens for elevational focus or defocusing: most ultrasound beams are focused in the elevational plane in order to sharpen the resolution of the target field. However, defocusing in the elevational plane can produce a type of volumetric image. This type of 3-dimensional image has no discrete information in the elevational plane. However, the superimposition of data can produce a 3-dimensional image of surfaces particularly if the surface insonated is viewed tangentially.

Multiplane phase-array transducer: multiplane technology usually refers to the technique of rotating a phased array transducer into multiple planes. This function imparts functionality of the image projection without the need of moving the catheter. The transducer array can be moved (i.e., rotated) in an longitudinal axis of the catheter which produces a partial or complete toroidal image (doughnut-shaped). If the transducer is rotated in an axis of the ultrasound beam, a conical (cone-shaped) field of view is produced. Rotating arrays are a means for obtaining a larger field information. By electronically (or by other means, such as mechanically, or chemically, or optically) coalescing out-of-field views, a 3-dimensional (volumetric) image can be obtained.

Further shown in FIG. 1, the ultrasonic transducer array 38 includes an end array 44 and a side array 46. The ultrasonic transducer end array 44 includes at least one row of ultrasonic transducer elements mounted on the elongated body 40 at a forward end 48. The ultrasonic transducer side array 46 also includes at least one row of ultrasonic transducer elements mounted on the elongated body 40 along a first side 50 of the elongated body 40. Each of the ultrasonic transducer elements of the side array 46 and the end array 44 are operable as a single ultrasound transducer which are phased to produce a field of side-and-end view.

Accordingly, the present invention provides a simultaneous end-view and side-view ultrasound imaging catheter (each array grouping can be simultaneously or individually viewed). The number of ultrasonic transducer elements and the size of each array can vary within the scope of the present invention. In a preferred embodiment, the side array 46 is more robust than the end array 44. In another embodiment, a more robust array is placed at the end than at a side. In certain applications, this embodiment may be more applicable. In further another embodiment, the end array 44 and the side array 48 are placed in the same manner. In some applications, this embodiment with equal distribution of groupings may be preferred. In certain applications, the output of each array or a portion of an array can be separately displayed and/or interrogated. This solution can provide better navigational and therapeutic visual aids. The various uses of the side-view and/or end-view are briefly discussed, but not limited, below:

Side view uses: this view is principally used to look at anatomy, procedures, and therapy adjacent to the longitudinal axis 42 of the catheter 20 or in remote fields extending far beyond the catheter 20.

End-view uses: most commonly, this view helps safely navigate the catheter tip within closed spaces or orifices. In addition, procedures or therapeutic interventions directly in front of the catheter can be observed or performed.

Simultaneous side-and-end view: this function fosters a wide field of view from within a confined space. This will assist an operator in navigation and more assuredly visualize events in a general environment around the catheter 20 as well as in remote cavities extending far beyond the catheter 20.

FIGS. 2A and 2B are transversal cross-sectional views of the catheter 20 of FIG. 1 along lines A—A and B—B, respectively.

In FIG. 3, an ultrasonic transducer array 52 includes an end array 54, a first side array 56, and a second side array 58. Similar to FIG. 1, the end array 54 includes at least one row of ultrasonic transducer elements mounted on the elongated body 40 at a forward end 48. The first side array 56 includes at least one row of ultrasonic transducer elements mounted on the elongated body 40 along a first side 50 of the elongated body 40. The second side array 58 includes at least one row of ultrasonic transducer elements mounted on the elongated body 40 along a second side 60 of the elongated body 40. Each of the ultrasonic transducer elements of the side arrays 56,58 and the end array 54 are operable as a single ultrasound transducer which are phased to produce a field of side-and-end view. Accordingly, the present invention provides a simultaneous end-view and side-view ultrasound imaging catheter (each array grouping can be simultaneously viewed or individually viewed for better navigational and therapeutic visual aids).

FIG. 4 is a transversal cross-sectional view of the catheter 20 of FIG. 3 along line C—C.

FIG. 3 shows the end array 54 and two side arrays 56,58 of the array 52 being disposed in a same plane. In FIG. 5, two ultrasonic transducer arrays 52 and 62 are disposed in two planes which form a biplanar field of side-and-end view. The array 62 can be similar to array 52 except that the array 62 is disposed transversely an angle from the array 52. In one embodiment, the array 62 also includes an end array and two side arrays. In an alternative embodiment, the array 62 can include an end array and one side array as shown in FIG. 1. In addition, each of the ultrasonic transducer elements of the arrays 52 and 56 can be operated as a single ultrasound transducer which are phased to produce the biplanar field of side-and-end view.

FIG. 6 is a transversal cross-sectional view of the catheter 20 of FIG. 5 along line D—D.

In FIG. 7, an ultrasonic transducer array 64 includes a plurality of ultrasonic transducer arrays like 52 or 62 which are mounted on the elongated body 40. Each of the ultrasonic transducer elements of the plurality of transducer arrays are operable as a single ultrasound transducer which are phased to produce a multiplanar omnidirectional field of side-and-end view.

FIG. 8 is a transversal cross-sectional view of the catheter 20 of FIG. 7 along line E—E.

FIGS. 7 and 8 illustrate that the ultrasonic transducer array 64 is arranged approximate all around the proximate end 48 of the catheter 20 which forms the multiplanar omnidirectional field of view. In other alternative embodiments, the ultrasonic transducer array may be arranged on a portion or several portions of the catheter 20 around the proximate end 48 which forms a multiplanar multi-directional field of view.

In addition, the above discussed different configurations of the arrays can be used in FIGS. 1–8. For example, a lens can be used to cover the array(s), or the array(s) can be rotated transversely along the longitudinal axis 42 of the catheter 20, or the array(s) can be rotated along an axis of the ultrasound beam, etc. It is appreciated to a person skilled in the art that a combination of two or more different configurations of the arrays can be used without departure from the principles and scope of the present invention.

Further in one embodiment, the ultrasonic transducer arrays may include a piezoelectric polymer material. It is appreciated that any other suitable types of materials can be used within the principles and scope of the present invention. For example, the ultrasonic transducer arrays may include a polyvinylidenedifloride (PVDF) material.

Furthermore in one embodiment, the ultrasonic transducer array may have a frequency of 5 to 30 MHz. It is appreciated that any other suitable frequencies can be used within the principles and scope of the present invention. For example, the ultrasonic transducer array may have a frequency of 7 to 15 MHz.

Thus, the preferred embodiment of the present invention has been described in detail. It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A catheter apparatus, comprising:
   an elongated flexible catheter body having a longitudinal axis;
   a first ultrasonic transducer side array having a row of ultrasonic transducer elements longitudinally mounted on the body along a first side of the body;
   an ultrasonic transducer end array having at least two rows of ultrasonic transducer elements mounted on the body at a forward end of the body;
   a second ultrasonic transducer side array having a row of ultrasonic transducer elements longitudinally mounted on the body along a second side of the body; and
   wherein the first ultrasonic transducer side array and the ultrasonic transducer end array are disposed in a first plane, the second ultrasonic transducer side array and the ultrasonic transducer end array are disposed in a second plane, the ultrasonic transducer elements of the first and second side arrays and the end array being operable as a single ultrasound transducer which are phased to produce a field of multi-planar side-and-end view.

2. A catheter apparatus of claim 1, wherein the ultrasonic transducer side and end arrays include a piezoelectric polymer material.

3. A catheter apparatus of claim 1, wherein the ultrasonic transducer side and end arrays include a polyvinylidenedifloride (PVDF) material.

4. A catheter apparatus of claim 1, wherein the ultrasonic transducer side and end arrays are sector phased arrays.

5. A catheter apparatus of claim 1, wherein the catheter body has a diameter of 4 to 15 French.

6. A catheter apparatus of claim 1, wherein the catheter body has a length 20 to 120 cm.

7. A catheter apparatus of claim 1, further comprising a third ultrasonic transducer side array having a row of ultrasonic transducer elements longitudinally mounted on the body along a third side of the body, wherein the third ultrasonic transducer side array, the first ultrasonic transducer side array, and the ultrasonic transducer end array are disposed in the first plane, the ultrasonic transducer elements of the first, second, and third side arrays and the end array are operable as a single ultrasound transducer.

8. A catheter apparatus of claim 7, further comprising a plurality of ultrasonic transducer side arrays to form a plurality of planes, wherein the ultrasonic transducer elements of the ultrasonic transducer side and end arrays are operable as a single ultrasound transducer which are phased to produce a multi-planar omnidirectional field of view.

* * * * *